United States Patent [19]
Francis

[11] Patent Number: 5,899,214
[45] Date of Patent: May 4, 1999

[54] DENTAL FLOSS DISPENSER AND APPLICATOR USED IN FIXED ORTHODONTIC APPLIANCES

[76] Inventor: Shlomo Francis, 6629 N. Francisco Ave., Chicago, Ill. 60645

[21] Appl. No.: 09/019,601

[22] Filed: Feb. 6, 1998

[51] Int. Cl.$^6$ .................................................. A61C 15/00
[52] U.S. Cl. ........................ 132/323; 132/324; 132/325; 132/326; 132/327
[58] Field of Search .................................. 132/322, 323, 132/324, 325, 326, 327

[56] References Cited

U.S. PATENT DOCUMENTS

| | | | |
|---|---|---|---|
| 2,554,526 | 5/1951 | Dembenski | 132/325 |
| 3,870,059 | 3/1975 | Bennington | 132/92 A |
| 3,896,824 | 7/1975 | Thornton | 132/89 |
| 4,326,547 | 4/1982 | Verplank | 132/89 |
| 4,364,380 | 12/1982 | Lewis | 128/89 |
| 4,637,412 | 1/1987 | Martinez | 132/323 |
| 4,657,034 | 4/1987 | Koski | 132/323 |
| 4,974,614 | 12/1990 | Selker | 132/321 |
| 5,050,625 | 9/1991 | Siekman | 132/323 |
| 5,052,420 | 10/1991 | Chen | 132/325 |
| 5,094,255 | 3/1992 | Ringle | 132/321 |
| 5,101,843 | 4/1992 | Peng | 132/323 |
| 5,176,157 | 1/1993 | Mazza | 132/325 |
| 5,184,631 | 2/1993 | Ikeda | 132/323 |
| 5,199,452 | 4/1993 | Cheng | 132/325 |
| 5,224,502 | 7/1993 | Walker | 132/325 |
| 5,415,188 | 5/1995 | Altshuler | 132/325 |
| 5,573,022 | 11/1996 | Winters | 132/325 |
| 5,613,508 | 3/1997 | Bushman | 132/325 |

OTHER PUBLICATIONS

"FlossPopper" product literature, GAC INternational, Inc.

*Primary Examiner*—John J. Wilson
*Assistant Examiner*—Trang Doan
*Attorney, Agent, or Firm*—Milton S. Gerstein

[57] ABSTRACT

A dental floss dispenser and applicator to be used with fixed orthodontic appliances, provided for a wearer to clean food, debris, and dental plaque so as to prevent proximal caries and periodontal disease. The dental flosser includes a handle section, a dental floss mounting section, and a single floss support portion wherein the dental floss mounting section and handle section contain a metered floss dispenser and locking means for floss being dispensed, and wherein the floss support contains a through hole to continuously supply floss. The floss support is slender so that it can be inserted into the narrow clearance between the adjacent surfaces of the teeth. The locking means holds the floss taught and allows for easy access to clean floss during operation.

17 Claims, 2 Drawing Sheets

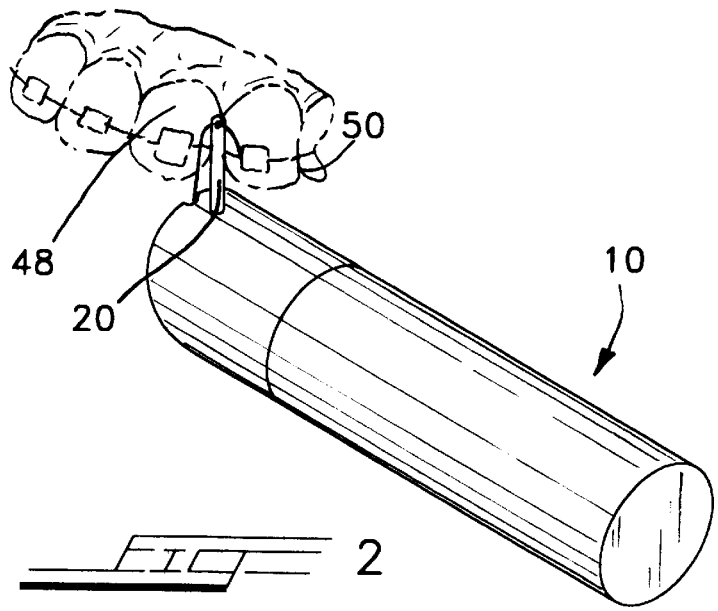
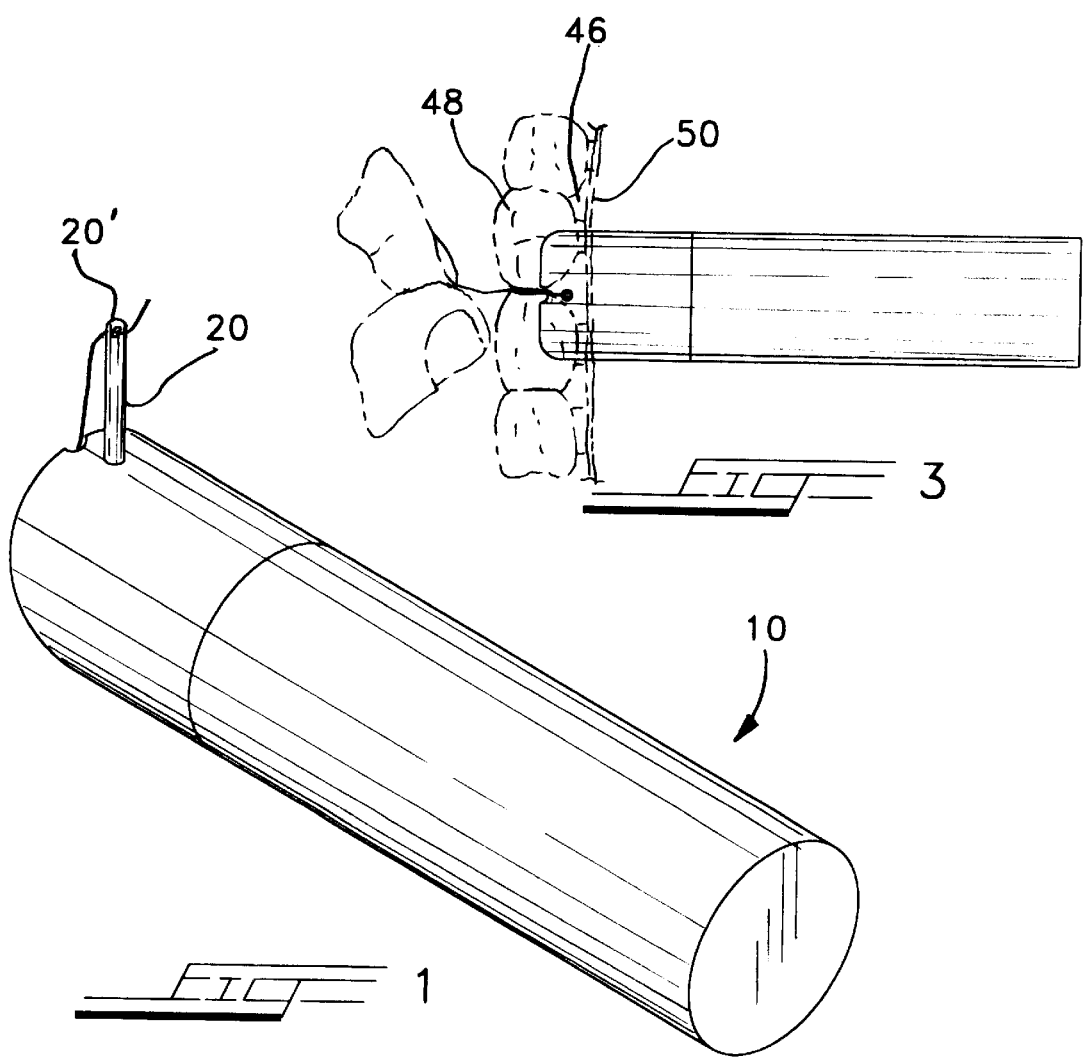

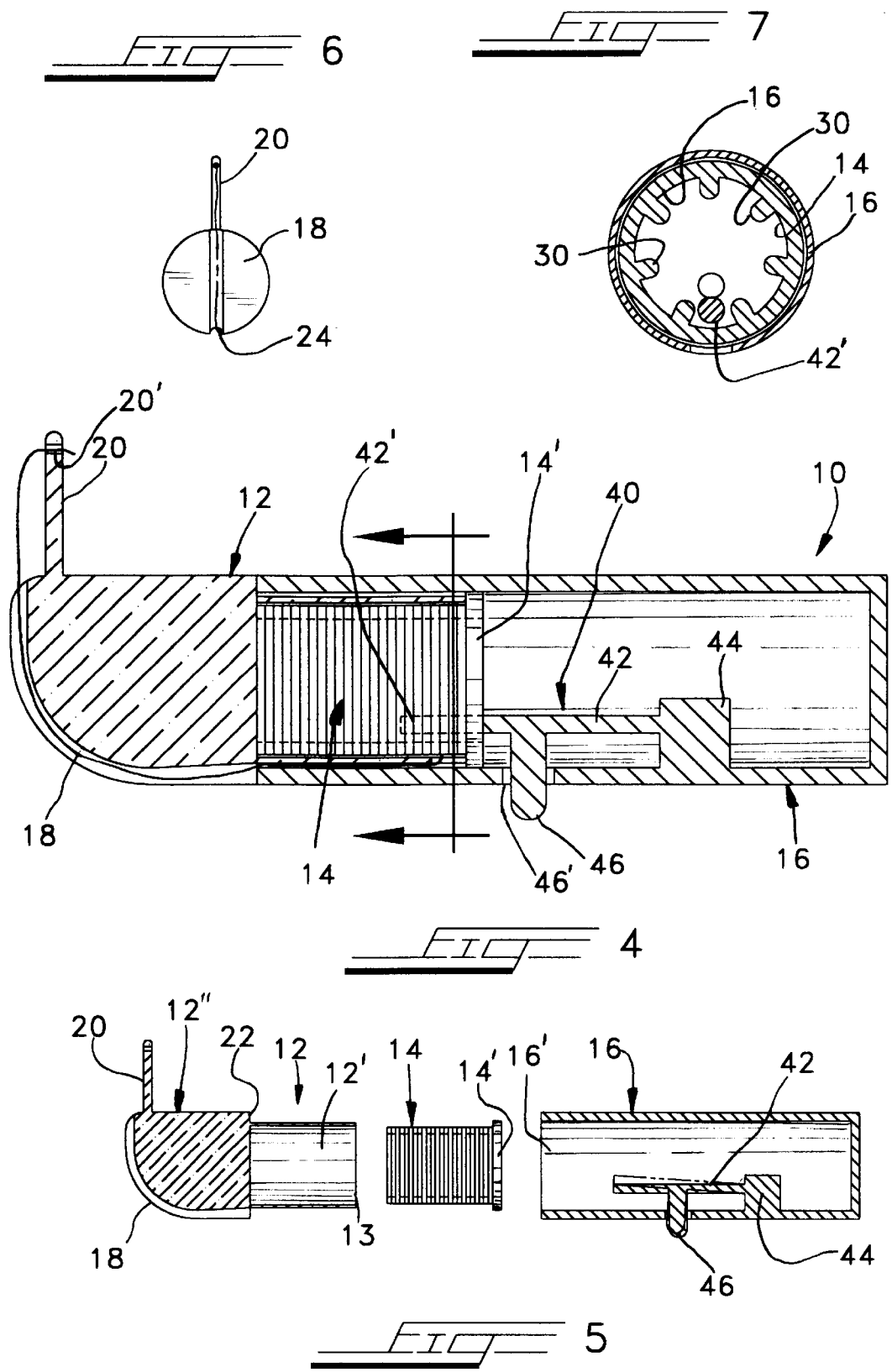

DENTAL FLOSS DISPENSER AND APPLICATOR USED IN FIXED ORTHODONTIC APPLIANCES

BACKGROUND OF INVENTION

The present invention relates to a dental floss dispenser and applicator used by patients with fixed orthodontic appliances. The dental flosser includes a floss support and a holder portion containing a metered floss dispenser. The floss support is specially designed for use with fixed orthodontic appliances.

A dental flosser is used in such a manner that the dental floss is intruded between the adjacent surfaces of two teeth and into the gingival sulcus and then the floss is urged to scrape the surfaces to dislodge and remove food debris and dental plaque. The dental flosser appears to be a most effective tool for cleaning the adjacent surfaces of the teeth in cooperation with the toothbrush. However, during the orthodontic treatment period, a fixed orthodontic appliance is applied to the patient and a metal orthodontic wire is fixed between the teeth so that the conventional flosser is unable to go between the teeth to perform the up and down, left and right scraping movement. In addition, the conventional dental flosser is not designed to accommodate the requirements of a patient under orthodontic treatment. The excessively thick floss supports cannot fit through the quite narrow clearance between the metal orthodontic wire and the adjacent surface of the teeth. (The clearance between the metal orthodontic wire and the adjacent surface of the teeth is referred hereinafter as "clearance".)

Attempts to provide dental flossers that are suitable for orthodontic patients have generally produced dental flossers that include two floss supports and a strand of floss suspended between them. This frees the user from the necessity of grasping the floss with his fingers, but has the decided disadvantage of restricting maneuverability within the clearance. All of the prior art had to be moved as one inflexible unit. The one post and a flexible floss design provide increased maneuverability and access within the clearance.

For example, U.S. Pat. No. 5,101,843 to Peng, and U.S. Pat. No. 5,184,631 to Ikeda and the FLOSSPOPPER brand dental flosser which is distributed by GAC, all disclose dental flossers of the two post design. This design suffers from a number of disadvantages:

(a) Since the prior art is maneuvered as one inflexible unit, it does not allow vertiginous maneuvering within the clearance. This limitation increases difficulty and decreases cleaning efficiency of flossing.

(b) An inflexible unit doesn't permit varying the degree of tautness of the floss. Tautly pulled floss injures gums more readily than gently suspended floss that can respond to the variable surface of the gum line. Indirectly applying pressure to the floss, through the floss supports decreases control over the force and extent of insertion of the floss further increasing the risk of injury to the gums.

(c) When the floss is suspended between two posts, one cannot exert maximum pressure to the floss because pressure is indirectly applied via the supports. This decreases the efficiency of its cleaning power.

(d) Since the prior-art flosser is maneuvered as one inflexible unit, it requires increased dexterity to properly insert the flosser into the tiny clearance, and at the same time concentrate on properly intruding the floss between the adjacent surfaces of two teeth. The increased time and effort can discourage the user from flossing as often and as thoroughly as desired.

(e) Since the prior art is maneuvered as one inflexible unit, it requires inordinate perseverance to clean the back teeth at the necessary 90 degree angle as the mouth does not open wide enough for proper access.

(f) The dexterity required to properly floss with prior art devices is beyond the capability of many juveniles who comprise the majority of orthodontic patients.

(g) The prior art makes no provision for replacing floss, so the entire apparatus must be disposed of after use, which measurably increases cost.

While the FLOSSPOPPER has the other disadvantages of the two-post flosser, it is not disposable. However, the floss must be threaded into several cavities prior to each use. Furthermore, plaque can accumulate within the cavity, thereby obstructing future re-threading. Furthermore, there is no locking mechanism for the floss, which must be grasped manually during the entire flossing process. It is extremely difficult to maintain one's grip on the floss when teeth are tightly wedged, therefore floss often requires repeated rethreading.

SUMMARY OF INVENTION

It is the object of the present invention to provide a flexible flosser with unrestricted maneuverability within the clearance, providing easier insertion and increased cleaning efficiency of flossing.

It is a further object of the invention to provide a flosser with improved flossing efficiency by allowing the finger to direct the pressure.

It is a further object of the invention to provide a flosser where the floss can be adjusted to varying degrees of tautness, as loosely suspended floss can respond to the variable surface of the gum line, thereby minimizing risk of injury to the gums.

It is a further object of this invention to provide a flosser which requires decreased time and effort to use and will encourage through and frequent cleaning.

The present invention further has as its object to provide a flosser that is easily maneuvered by juveniles, even to the back teeth.

It is the further object of the invention to provide a flosser in which clean floss can be easily accessible during flossing.

It is the further object of the invention to provide a simple and economical locking dispenser for ease of use and economy of manufacture.

It is the further object of the invention to provide an economical, nondisposable, continuously feeding, metered and locking floss dispenser and applicator that eliminates the need for constant re-threading. Further objects and advantages of my invention will become apparent from a consideration of the drawings and ensuing description.

BRIEF DESCRIPTION OF THE DRAWINGS

FIG. 1 is a perspective view of the invention containing a strand of dental floss therein;

FIG. 2 is a perspective view thereof showing the single post of the dental flosser of the invention in use for flossing teeth;

FIG. 3 is a top view of FIG. 2;

FIG. 4 is a longitudinal cross-sectional view of FIG. 1;

FIG. 5 is an assembly view, in cross section;

FIG. 6 is a left end view of FIG. 4; and

FIG. 7 is a cross-sectional view taken along line 7—7 of FIG. 4.

DETAILED DESCRIPTION OF PREFERRED EMBODIMENT

Referring now to the drawings, there is shown the dental flosser 10 of the invention. The dental flosser is made up of three main components, as best seen in FIG. 5: A first, dental-floss mounting and dispensing section 12, a dental-floss supply or reel 14, and a second, outer main cover or housing section 16. The first section 12 defines a substantially cylindrically-shaped, partially-hollow interior portion 12' in which the supply of dental floss 14 is received, and also defines another forwardly-located portion 12" having a smooth, curved lower outer surface 18 against which the exiting dental floss contacts during dispensing. Projecting from the upper surface of the first section is a single, upstanding floss-receiving post 20 provided with an upper through-hole or opening 20' through which is threaded the dental floss. The portion 12' has a smaller diametric extent than the portion 12" to define an annular shoulder 22 against which the end 16' of the housing section 16 abuts when the device 10 is fully assembled. The exterior diameter of the portion 12' is less than the interior diameter of the housing section 16, so that the housing section is partially telescopingly-mounted about the portion 12' in a manner that allows the thread to exit and be dispensed in the annular volume between the exterior surface of the portion 12' and the interior surface of the housing section 16, in the manner described hereinbelow. The outer surface 18 of the forwardly-located portion 12" is provided with an elongated, longitudinally-extending groove or channel 24, as best seen in FIG. 6, in which runs the dental floss as it approaches the single post 20. As the dental floss is dispensed, or unwound from the supply reel 14, it exits from the open end of the interior portion 12', and travels along the groove 24 and passes through the opening 20' of the post 20. The depth of the groove 24 is such that the bottom section thereof is coextensive with the lower annular volume defined between the interior annular wall of the housing section 16 and the exterior surface of the section 12', so that the floss may pass unobstructed from the reel to the groove. There also may be provided a cutout on the end-edge 13 of the section 12 through which the floss may pass on its way to the groove 24, so that sharp turns and edges may be obviated in order to prevent the inadvertent cutting of the floss.

Mounted within the portion 12' is the dental floss supply or reel 14. This supply may be in reel or other form, and is preferably held therein to allow for rotational movement as the dental floss is dispensed. The reel 14 is a simple spool, or the like, about which the floss is wound, although other structures may be used, or just a simple ball of the floss may be used with a reel, as long as the ball is allowed adequate movement during dispensing. The reel 14 has a hollow interior and an annular end-flange 14'. The end-flange has a greater diametric extent than the main body of the reel or spool 14, which outer diameter is approximately equal to the inner diameter of the housing section 16, as best seen in FIG. 4, so as to provide a friction-fit between the outer surface of the end-flange 14' and the inner surface of the housing section 16. This force-fit allows the housing section to be retained in place when using the device, yet allows for easy opening of the device by sliding the housing section 16 away from the first section 12, in order to allow for replacing the reel 14. Other conventional structure may be used for achieving the releasable connection between the outer housing and the portion 12'. The reel 14 is provided interiorly thereof with a plurality of detents or protuberances 30, there being, for example, seven such detents, as seen in FIG. 7, although more or less may be used, which together form a ratchet wheel. The detents 30 are equi-angularly spaced apart and project from the inner surface of the reel 14. The detents 30 are used to prevent rotation of the reel 14 when the device is being used to floss the teeth by means of a pawl mechanism 40 mounted in the interior of the housing section 16. The pawl-mechanism 16 is comprised of an elongated, resilient lever-arm 42 anchored to the interior of the housing section 16 by means of an anchor or post 44. The arm 42 may be made of resilient thermoplastic material, or other, well-known flexible material that allows the pivotal movement of the arm relative to the anchor 44. The lever-arm 42 extends a great enough distance parallel to the longitudinal axis of the housing section 16 so as to protrude into the interior of the reel 14, as seen in FIG. 4. Protruding from a mid-section of the lever-arm 42 is a button or dowel 46 that protrudes outwardly from the interior of the interior of the housing section 16 by means of a hole or opening 46' provided in the housing section. When the device 10 is being used to floss trhe teeth, the lever-arm is positioned as shown in FIG. 4, with the button 46 protruding fully outwardly through the hole 46', and with the end 42' of the lever-arm 42 being located between two adjoining detents 30 of the interior of the reel, as seen in FIG. 7, whereby rotation of the reel is prevented. When new floss is to be dispensed, one simply depresses the button 46 inwardly to force the lever-arm 42 more interiorly into the housing section, which thereby displaces the end 42' to a region that does not intersect with the detents 30, whereby free rotation of the reel is allowed in order to dispense the floss.

FIGS. 2 and 3 show the device 10 in working position. The user is to grasp the loose end of floss with his finger. The floss support or post 20 can then be inserted into the clearance 46 between the teeth 48 and the arch wire 50. The dental floss is then intruded between the adjacent surfaces of the two teeth by alternating pressure between the two ends of the floss. Clean floss is easily dispensed during flossing by pressing the button 40. Since the end of the floss is held by the user, and not by another post as in the prior-art devices, the amount of tension applied to the floss may be varied at all times during the flossing. Furthermore, the end of the floss may be manuevered to any desired orientation that more efficiently effects the flossing of the teeth, which the prior-art devices with two fixed posts cannot achieve.

While this invention has been explained in relation to its preferred embodiment, it is to be understood the various modification thereof will be apparent to those skilled in the art upon reading this specification. For example, the flosser can be used with or without the dispenser, and the locking dispenser shown in the preferred embodiment can be substituted with many known methods of securing floss including manual securing. Therefore, it is to be understood that the invention disclosed herein is intended to cover all such modifications as shall fall within the scope of the appended claims.

What I claim is:

1. A dental flossing device for dispensing dental floss for use by persons having a fixed orthodontic appliance, comprising:
   a main housing comprising a first handle section and a second dental floss mounting section, said second section having a hollow interior for mounting a reel of dental floss, said main housing having a bottom surface and a front surface each of said first and second sections comprising cooperating means for connecting said first and second section; dental floss reel means having dental floss thereon, mounted in said second section for allowing rotational motion to said dental floss reel-means;

said main housing comprising an exit opening through which a section of said dental floss may exit to exteriorly thereof;

said main housing further comprising an upstanding dental-floss support means having a through-opening through which a section of said dental floss is threaded; rachet means for preventing the rotation of said dental floss reel-means, said rachet means comprising a plurality of teeth provided on said dental floss reel-means, pawl means mounted to said first section, and means for releasing said pawl means in order to allow said dental floss reel-means to freely rotate;

said main housing further comprising groove means for directing the dental floss exiting from said exit opening to said dental floss support means; said groove means comprising a first portion extending along the bottom surface of said main housing and a second portion extending along the front surface of said main housing between said first portion and said dental-floss support means, whereby the dental floss from said reel means is directed along said groove means to said support means and substantially retained therein as said dental floss is dispensed from said reel means.

2. The dental flossing device for dispensing dental floss for use by persons having a fixed orthodontic appliance, according to claim 1, wherein said dental-floss support means is mounted to a portion of the upper surface of said second section, said support means having a bottom end connected to said portion of the upper surface in close juxtaposition to the upper end of said second portion of said groove means.

3. The dental flossing device for dispensing dental floss for use by persons having a fixed orthodontic appliance, according to claim 2, wherein said dental-floss support means comprises a single, upstanding shaft, whereby the free end of the floss extending through said through-opening of said support means is gripped by one hand, while said main housing is gripped by another hand, with the floss between said through-opening and said free end held by the first hand being used for flossing the teeth of a person having a fixed orthodontic appliance.

4. A dental flossing device for dispensing dental floss for use by persons having a fixed orthodontic appliance, comprising:

a main housing having a hollow interior for containing a supply means of dental floss interiorly therein;

said dental floss supply means having dental floss thereon, contained in said main housing for allowing floss to be dispensed from said supply means;

said main housing comprising an upstanding dental-floss support means having a through-hole through which a section of said dental floss is threaded, wherein said dental floss can be continuously dispensed through said through-hole and not require rethreading;

said main housing comprising a first dental-floss mounting section in which is mounted said supply means, said supply means comprising a main body portion about which said dental floss is provided;

said supply means further comprising abutting means for abutting contact against the end of said first mounting section in order to limit insertion of said supply means in said first mounting section;

said abutting means comprising an annular flange at one end of said supply means, said annular flange having a diametric extent greater than the diametric extent of the opening of said first mounting section;

said housing comprising a second section having a hollow interior greater than the diametric extent of said abutting means, whereby said second section is telescopingly mounted about said supply means and a portion of said first mounting section.

5. The dental flossing device for dispensing dental floss for use by persons having a fixed orthodontic appliance, according to claim 4, wherein said main housing comprises securing means for securing the dental floss being supplied from said supply means.

6. The flossing device for dispensing dental floss for use by persons having a fixed orthodontic appliance, according to claim 5, wherein said securing means comprises a ratchet means for preventing the rotation of said dental floss supply means, said ratchet means comprising at least one tooth provided on said dental floss supply means, pawl means mounted interiorly of said main housing, and means for releasing said pawl means in order to allow said dental floss supply means to freely rotate.

7. The dental flossing device for dispensing dental floss for use by persons having a fixed orthodontic appliance, according to claim 4, wherein said main housing comprises groove means for directing the dental floss exiting from interiorly of said main housing to said through hole of said dental-floss support; said groove means having a depth in said main housing so that at least the bottom section of said groove means is substantially coextensive with the annular volume between said mounting section and said second section, said floss passing through said annular volume on its passage to said groove means.

8. The dental flossing device for dispensing dental floss for use by persons having a fixed orthodontic appliance, according to claim 7, wherein said groove means comprises a first portion extending along a portion of the bottom surface of said main housing, and a second portion extending along a portion of the front surface of said main housing whereby the dental floss from said supply means is directed along said groove means to said support means and substantially retained therein by said through-hole as said dental floss is dispensed from said supply means.

9. The dental flossing device for dispensing dental floss for use by persons having a fixed orthodontic appliance, according to claim 6, wherein said at least one tooth is formed in the interior thereof; said pawl means comprising a cantilevered arm having a free end, said free end having a detent for engagement with said at least one tooth, said cantilevered arm being pivotal for removing engagement of said detent with said at least one tooth in order to allow free rotation of said supply means for the dispensing thereof.

10. The dental device for dispensing dental floss for use by persons having a fixed orthodontic appliance, according to claim 9, wherein said cantilevered arm is mounted to the interior surface of said main housing.

11. The dental flossing device for dispensing dental floss for use by persons having a fixed orthodontic appliance, according to claim 10, wherein said main housing comprises an opening; said means for releasing said pawl means in order to allow said dental floss supply means to freely rotate comprising actuating means mounted to said cantilevered arm, and protruding through said opening for access thereto from exterior of said main housing, whereby, upon the inward pushing of said integral actuation means in said opening, said detent means of said cantilevered arm is released from engagement with said at least one tooth, to thereby allow for the free rotation of said supply means.

12. A method of using a dental flossing device for use by persons having a fixed orthodontic appliance, which dental flossing device has a main housing, said main housing having a single upstanding dental floss support means having a though-hole mounted to a forwardly-located upper surface of the main housing, though which a section of said dental floss is threaded, said method comprising:

(a) extending a first end of the floss through the through-hole of the upstanding dental-floss support means and securing a second end of the floss;

(b) gripping by at least one finger of a hand the first end of the dental floss;

(c) utilizing the section of the dental floss between the at least one finger gripping the first end of the dental floss and the through-hole for flossing the teeth;

(d) said step (c) comprising inserting said upstanding dental-floss support means in between the teeth to be flossed and the fixed orthodontic appliance, and positioning the finger holding the end of the dental floss interiorly in the mouth rearwardly of the teeth; and (e) said step (c) comprising using the section of the dental floss between the at least one finger gripping the end of the dental floss and the through-hole for flossing the teeth without obstruction by the fixed orthodontic device;

(f) said step (c) further comprising forcing the section of the dental floss between the at least one finger gripping the first end of the dental floss and the through-hole upwardly between two adjacent teeth;

(g) said step (c) further comprising utilizing said finger to control the force and extent of said insertion, whereby the risk of injury to the gums is reduced;

(h) maneuvering the support means within the clearance without restriction by the positioned floss, whereby floss is readily urged to perform desired right and left, up and down scraping motions.

13. A dental flossing device for dispensing dental floss for use by persons having a fixed orthodontic appliance, comprising:

a main housing having a hollow interior for containing a reel-means of dental floss interiorly therein;

dental floss reel means having dental floss mounted by said main housing for allowing rotational motion to said dental floss reel means;

said main housing further comprising an upstanding dental-floss support means having a through-opening through which a section of said dental floss is threaded; and ratchet means for preventing the rotation of said dental floss reel means, said ratchet means comprising at least one tooth provided on said dental floss reel means, pawl means mounted, and means for releasing said pawl means in order to allow said dental floss reel-means to freely rotate;

said at least one tooth being formed in the interior thereof;

said pawl means comprising a cantilevered arm having a free end, said free end having a detent for engagement with said at least one tooth, said cantilevered arm being pivotal for removing engagement of said detent with said at least one tooth in order to allow free rotation of said reel means for the dispensing thereof.

14. The dental flossing device for dispensing dental floss for use by persons having a fixed orthodontic appliance, according to claim 13, wherein said main housing comprises a first handle section and a second dental-floss mounting section, said second section having a hollow interior for mounting the reel means of dental floss; said cantilevered arm being mounted to the interior surface of said first section.

15. The dental flossing device for dispensing dental floss for use by persons having a fixed orthodontic appliance, according to claim 14, wherein said first section comprises an opening; said means for releasing said pawl means in order to allow said dental floss reel-means to freely rotate comprising actuation means mounted to said cantilevered arm, and protruding through said opening for access thereto from exterior of said main housing, whereby, upon the inward pushing of said integral actuation means in said opening, said detent means of said cantilevered arm is released from engagement with said at least one tooth, to thereby allow for the free rotation of said reel means.

16. A dental flossing device for dispensing dental floss for use by persons having a fixed orthodontic appliance, comprising:

a main housing having a hollow interior for containing a supply means of dental floss interiorly therein;

said dental floss supply means having dental floss contained in said main housing for allowing floss to be dispensed from said supply means;

said main housing comprising an upstanding dental-floss support means-hole through which a section of said dental floss passes, wherein said dental floss can be continuously dispensed;

said main housing comprising a first dental-floss mounting section in which is mounted said supply means, and a second section having a hollow interior greater than the diametric extent of at least a portion of said first mounting section, whereby said second section is telescopingly mounted about a portion of said first mounting section;

said main housing comprising groove means for directing the dental floss exiting from interiorly of said main housing to said dental-floss support, said groove means having a depth in said main housing so that at least the bottom section of said groove means is substantially coextensive with the annular volume between said first mounting section and said second section, said floss passing through said annular volume on its passage to said groove means.

17. The dental flossing device for dispensing dental floss for use by persons having a fixed orthodontic appliance, according to claim 16, wherein said groove means comprises a first portion extending along a portion of the bottom surface of said main housing, and a second portion extending along a portion of the front surface of said main housing, whereby the dental floss from said supply means is directed along said groove means to said support means and substantially retained therein as said dental floss is dispensed from said supply means.

* * * * *